(12) United States Patent
Mobley et al.

(10) Patent No.: US 9,138,087 B2
(45) Date of Patent: Sep. 22, 2015

(54) UNIVERSAL PRONE/SUPINE PILLOW

(71) Applicant: Latitude Innovations, Knoxville, TN (US)

(72) Inventors: Edward Mobley, Knoxville, TN (US); Eric Cox, Knoxville, TN (US); Tracy Thompson, Knoxville, TN (US)

(73) Assignee: Latitude Innovations, Knoxville, TN (US)

(*) Notice: Subject to any disclaimer, the term of this patent is extended or adjusted under 35 U.S.C. 154(b) by 0 days.

(21) Appl. No.: 14/175,472

(22) Filed: Feb. 7, 2014

(65) Prior Publication Data

US 2015/0223622 A1    Aug. 13, 2015

(51) Int. Cl.
*A47C 20/00* (2006.01)
*A47G 9/10* (2006.01)

(52) U.S. Cl.
CPC .............. *A47G 9/1054* (2013.01); *A47G 9/10* (2013.01); *A47G 9/109* (2013.01); *A47G 2009/1018* (2013.01)

(58) Field of Classification Search
CPC ..... A47G 9/1054; A47G 9/10; A47G 9/1009; A47G 2009/1018; A47G 9/109
USPC ............. 5/622, 636, 637, 638, 639, 640, 643, 5/645
See application file for complete search history.

(56) References Cited

U.S. PATENT DOCUMENTS

| | | | |
|---|---|---|---|
| 2,700,779 A | 2/1955 | Tolkowsky | |
| 2,782,427 A | 2/1957 | Ericson | |
| 5,097,551 A | 3/1992 | Smith | |
| 5,479,667 A | 1/1996 | Nelson et al. | |
| 5,613,501 A * | 3/1997 | Michelson | 5/637 |
| 5,644,809 A | 7/1997 | Olson | |
| 5,906,205 A | 5/1999 | Hiebert | |
| 5,953,777 A * | 9/1999 | Buck | 5/636 |
| D414,974 S * | 10/1999 | Marrone et al. | D6/601 |
| 5,960,494 A * | 10/1999 | Gilliland et al. | 5/638 |
| 5,987,676 A * | 11/1999 | Littleford et al. | 5/636 |
| 6,003,177 A * | 12/1999 | Ferris | 5/636 |
| 6,006,380 A * | 12/1999 | Sramek | 5/636 |
| 6,065,166 A | 5/2000 | Sharrock et al. | |
| 6,345,401 B1 * | 2/2002 | Frydman | 5/636 |
| D456,516 S * | 4/2002 | Cheshaek et al. | D24/183 |
| 6,490,737 B1 * | 12/2002 | Mazzei et al. | 2/410 |
| 6,490,742 B2 * | 12/2002 | Hall et al. | 5/630 |
| 6,637,058 B1 * | 10/2003 | Lamb | 5/638 |
| 6,745,418 B1 * | 6/2004 | Turner, Jr. | 5/638 |
| 6,749,159 B1 * | 6/2004 | Hess | 248/118 |
| 6,842,924 B1 * | 1/2005 | Walters | 5/637 |
| 6,895,619 B1 * | 5/2005 | Lee | 5/636 |
| 6,976,280 B2 * | 12/2005 | Coutts | 5/636 |
| 7,441,293 B1 | 10/2008 | Singer et al. | |
| 7,634,828 B2 | 12/2009 | Elhabashy | |

(Continued)

*Primary Examiner* — Peter M Cuomo
*Assistant Examiner* — David E Sosnowski
(74) *Attorney, Agent, or Firm* — Pitts & Lake, P.C.

(57) ABSTRACT

A universal pillow to accommodate a head of a patient in a prone and in a supine position, including a support surface having a frontal/parietal support portion, a mental/occipital support portion, and two side portions extending between respective ends of the frontal/parietal and mental/occipital support portions, a recessed head receiving portion, provided in the support surface, configured to be lower than the frontal/parietal support portions, mental/occipital support portions, and side portions, and having an opening configured to receive at least a portion of a face of the patient, and a bottom surface disposed opposite to the support surface.

11 Claims, 2 Drawing Sheets

(56) References Cited

U.S. PATENT DOCUMENTS

| | | | |
|---|---|---|---|
| 7,810,192 B2* | 10/2010 | Fujita et al. | 5/636 |
| 7,856,687 B2* | 12/2010 | Chou | 5/640 |
| 8,020,229 B2* | 9/2011 | Sato | 5/636 |
| 8,234,732 B2* | 8/2012 | Bacon | 5/636 |
| 8,418,294 B1* | 4/2013 | Davis | 5/640 |
| 8,468,628 B1* | 6/2013 | Cheng | 5/641 |
| 8,549,683 B2* | 10/2013 | Ratner | 5/638 |
| 8,732,877 B2* | 5/2014 | Ramp | 5/632 |
| 8,769,745 B1* | 7/2014 | Lin | 5/638 |
| 2002/0184707 A1* | 12/2002 | Stevens | 5/640 |
| 2006/0053556 A1* | 3/2006 | Piontek | 5/637 |
| 2006/0150336 A1* | 7/2006 | Jackson | 5/644 |
| 2008/0034504 A1* | 2/2008 | Schmidt | 5/644 |
| 2008/0134437 A1 | 6/2008 | Small | |
| 2009/0025146 A1* | 1/2009 | Mazzei et al. | 5/643 |
| 2010/0205743 A1* | 8/2010 | Harges | 5/638 |
| 2011/0162146 A1* | 7/2011 | Frydman | 5/639 |
| 2011/0247140 A1* | 10/2011 | Nakayama et al. | 5/640 |
| 2012/0073056 A1* | 3/2012 | Freund et al. | 5/639 |
| 2012/0144591 A1* | 6/2012 | Mobley et al. | 5/640 |
| 2012/0284924 A1* | 11/2012 | Pratt et al. | 5/640 |
| 2013/0205504 A1* | 8/2013 | Ratner | 5/622 |
| 2013/0298333 A1* | 11/2013 | Chen | 5/636 |
| 2013/0305456 A1* | 11/2013 | Thompson | 5/632 |
| 2014/0053337 A1* | 2/2014 | Mac Marbury, III | 5/638 |
| 2014/0245539 A1* | 9/2014 | Ooba | 5/636 |
| 2014/0317851 A1* | 10/2014 | Hammack et al. | 5/640 |

* cited by examiner

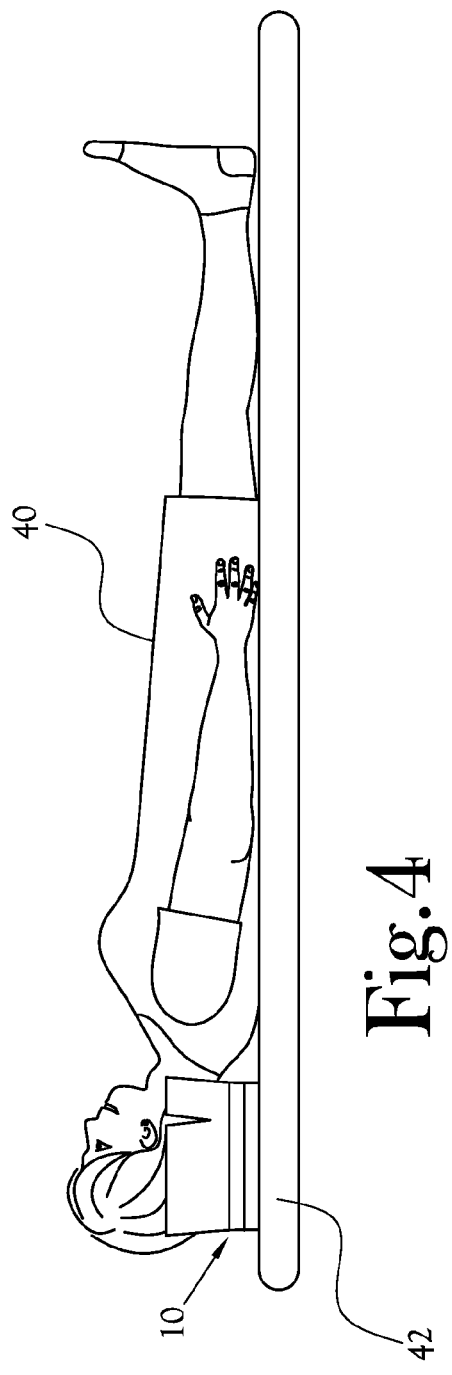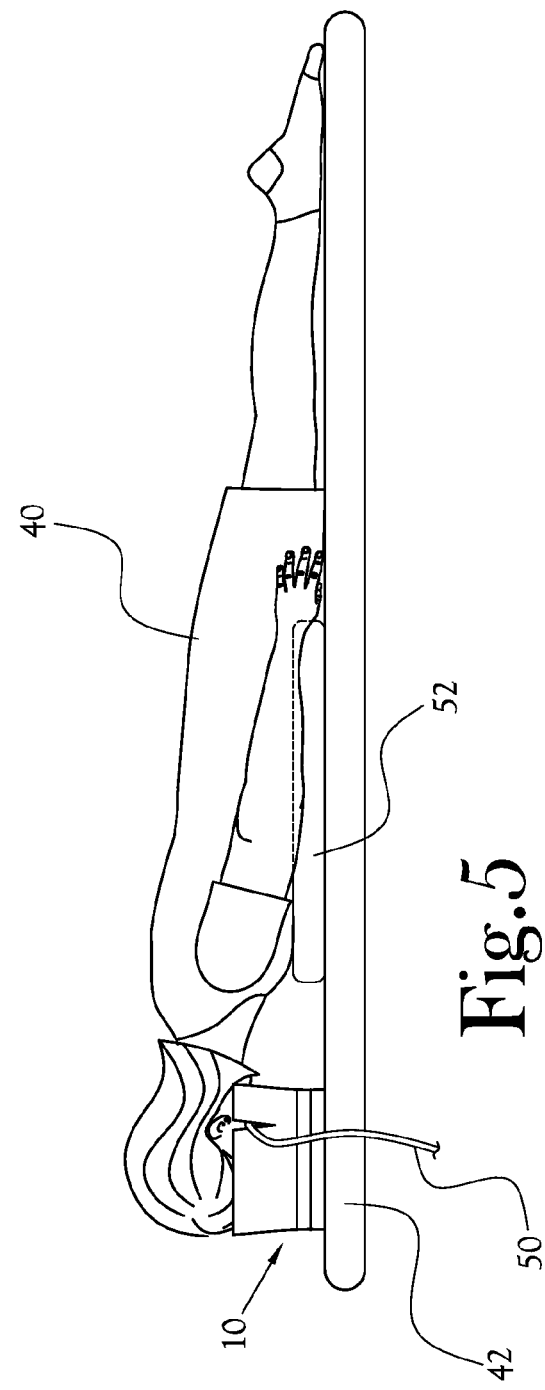

UNIVERSAL PRONE/SUPINE PILLOW

CROSS-REFERENCE TO RELATED APPLICATIONS

Not Applicable

FIELD OF INVENTION

The present general inventive concept relates generally to medical support devices, and, more particularly, to an adjustable pillow to support a patient's head at a variety of positions and heights.

BACKGROUND

The controlled positioning of patients is of significant importance in many surgical and convalescence procedures. Pillows or rolls contoured with special shapes have been developed to support a patient in one or more positions on an operating table during and/or after surgery.

In many examples during surgery and/or convalescence, a patient may desire or be required to rest in the face-down, or prone, position or the face-up, or supine, position. It would be desirable to have a pillow to provide comfortable support to the patient in both positions, and one which is cost-effective and disposable with each use to reduce possible patient cross-contamination.

Further problems with pillows or other support devices made of gel or other materials include the inability to readily adjust the height of the pillow according to the needs of various patients to adequately relieve pressure points from the patient contact/position, to readily clean and maintain proper hygienic properties, to prevent slippage of the cushion, sliding of the patient, and so on.

BRIEF SUMMARY

The present general inventive concept provides a universal pillow to accommodate the head of a patient in a prone and/or supine position. According to various example embodiments of the present general inventive concept, removable base layers may be provided to adjust the height and/or angle of the top surface of the universal pillow.

Additional features of the present general inventive concept will be set forth in part in the description which follows, and, in part, will be obvious from the description, or may be learned by practice of the present general inventive concept.

Example embodiments of the present general inventive concept may be achieved by providing a universal pillow to accommodate a head of a patient in a prone and in a supine position, including a support surface having a frontal/parietal support portion, a mental/occipital support portion, and two side portions extending between respective ends of the frontal/parietal and mental/occipital support portions, a recessed head receiving portion, provided in the support surface, configured to be lower than the frontal/parietal support portions, mental/occipital support portions, and side portions, and having an opening configured to receive at least a portion of a face of the patient, and a bottom surface disposed opposite to the support surface.

The opening in the recessed head receiving portion may extend through the bottom surface.

The opening in the recessed head receiving portion may include an orbital opening and/or an oral/nasal opening.

The opening may include an orbital opening and an oral/nasal opening, the oral/nasal opening being substantially perpendicular to the orbital opening.

The universal pillow may further include access slits provided in the side portions to allow access to the patient for one or more medical devices.

The universal pillow may further include one or more removable base layers provided to the bottom surface to adjust a height of the universal pillow.

The support surface, recessed head receiving portion, bottom surface, and/or removable base layers may be formed from a foam material having a high coefficient of friction to inhibit slippage therebetween.

The one or more removable base layers may be coupled to the bottom surface in a stack such that a first removable base layer is coupled to the bottom surface, and any additional removable base layers are coupled to an adjacent removable base layer.

The removable base layers may be coupled to the bottom surface and/or one another by an adhesive compound.

The removable base layers may be coupled to the bottom surface and/or one another by protruding and/or receiving portions provided to the bottom surface and removable base layers.

The universal pillow may be formed of a foam fabricated from polyurethane foam, foam rubber, XPS foam, polystyrene, phenolic material, or any combination thereof, including a closed cell foam.

Other features, aspects, and embodiments of the present general inventive concept will be apparent from the following detailed description, the drawings, and the appended claims.

BRIEF DESCRIPTION OF THE FIGURES

The following example embodiments are representative of example techniques and structures designed to carry out the objects of the present general inventive concept, but the present general inventive concept is not limited to these example embodiments. In the accompanying drawings and illustrations, the sizes and relative sizes, shapes, and qualities of lines, entities, and regions may be exaggerated for clarity. A wide variety of additional embodiments will be more readily understood and appreciated through the following detailed description of the example embodiments, with reference to the accompanying drawings in which:

FIGS. 4-5 illustrate example uses of the universal pillow of FIGS. 1-3.

DETAILED DESCRIPTION

Figure 2:
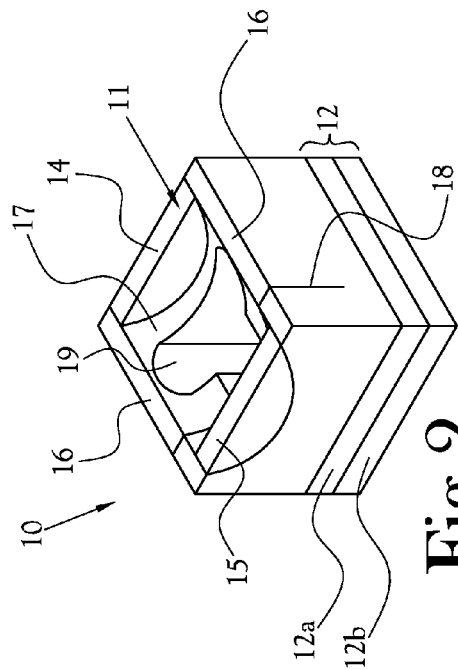
FIGS. 1-3 illustrate a universal prone/supine pillow according to an example embodiment of the present general inventive concept.

Reference will now be made to various example embodiments of the present general inventive concept, examples of which are illustrated in the accompanying drawings and illustrations. The example embodiments are described herein in order to explain the present general inventive concept by referring to the figures.

The following detailed description is provided to assist the reader in gaining a comprehensive understanding of the methods, apparatuses, and/or systems described herein. Accordingly, various changes, modifications, and equivalents of the methods, apparatuses, and/or systems described herein will be suggested to those of ordinary skill in the art. The described progression of processing operations described are merely examples, however, and the sequence of operations is not limited to that set forth herein and may be changed as is known in the art, with the exception of operations necessarily occurring in a certain order. Also, description of well-known functions and constructions may be omitted for increased clarity and conciseness.

Note that spatially relative terms, such as "up," "down," "right," "left," "beneath," "below," "lower," "above," "upper" and the like, may be used herein for ease of description to describe one element or feature's relationship to another element(s) or feature(s) as illustrated in the figures. Spatially relative terms are intended to encompass different orientations of the device in use or operation in addition to the orientation depicted in the figures. For example, if the device in the figures is turned over or rotated, elements described as "below" or "beneath" other elements or features would then be oriented "above" the other elements or features. Thus, the exemplary term "below" can encompass both an orientation of above and below. The device may be otherwise oriented (rotated 90 degrees or at other orientations) and the spatially relative descriptors used herein interpreted accordingly.

Various example embodiments of the present general inventive concept, as described herein, provide a universal pillow that allows a patient to rest comfortably thereon in a variety of positions, including, but not limited to, prone and supine positions. Various example embodiments of the present general inventive concept also provide such a universal pillow with a height that can be adjusted by detaching or attaching one or more separately formed base portions of the pillow. In various example embodiments, the one or more separately formed base portions may be configured to have substantially the same length and width as the pillow to which the base portions are attached. Also, it is understood that the term "pillow" is used in a general sense, and may be referred to as a cushion, headrest, etc.

In various example embodiments, the universal pillow may be fabricated from a foam material with a high static coefficient of friction. Generally, the foam material is compressible or elastomeric. In various example embodiments, a closed-cell foam may be used. Various example embodiments may include a foam fabricated from polyurethane foam, foam rubber, XPS foam, polystyrene, or phenolic material, but the present general inventive concept is not limited to any particular type of foam material. A foam material may lend various benefits, both economic and practical, over conventional positioning means, such as gel-based devices.

Figure 3:
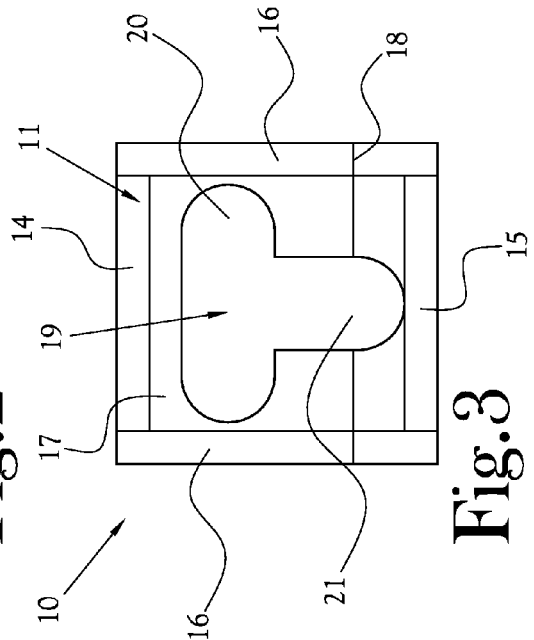
Figure 1:
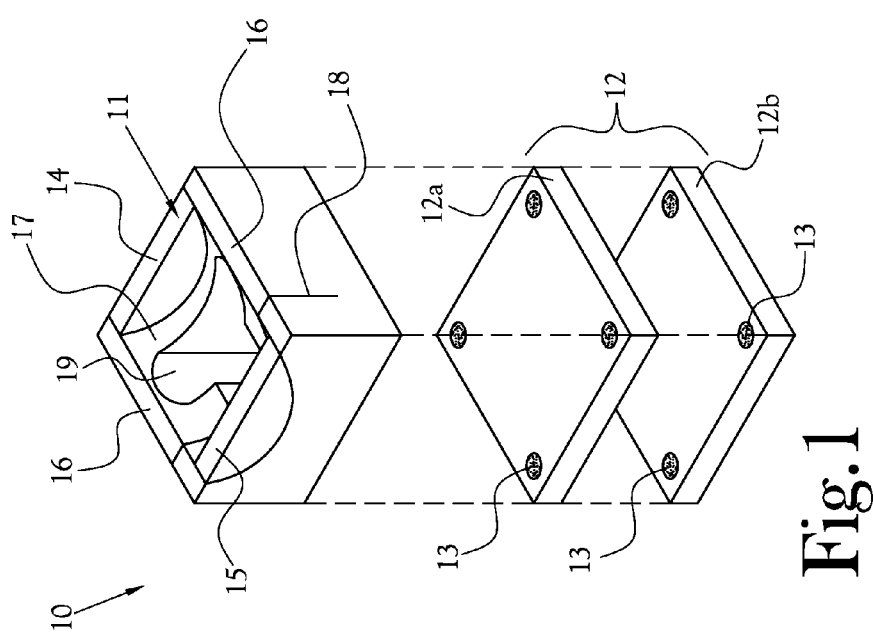

FIGS. 1-3 illustrate a universal prone/supine pillow according to an example embodiment of the present general inventive concept. It is understood that the pillow is referred to in a general sense as a universal prone/supine pillow, but the use of the pillow is not limited to such positions. For instance, the universal pillow may be used to support a patient's head while the patient lies on his/her side, or other such positions. Also, the universal pillow may be used to support body parts other than the head of a patient.

In the example embodiment illustrated in FIGS. 1-3, the universal prone/supine pillow 10 includes a support surface 11 at the top of the pillow 10 to generally support the head of the patient, and two removable and separately formed base layers 12 configured to have substantially the same length and width as the underside of the upper portion of the pillow 10, the base layers 12 being attached to the underside of the pillow 10 in a detachable manner. It is noted that while two removable base layers 12a and 12b are illustrated in the example embodiment of FIGS. 1-3, various other example embodiments may only include one base layer 12, or three or more base layers 12, to allow fewer or more height options for the pillow 10, and in some example embodiments no removable base layers 12 may be provided. In various example embodiments, one of the base layers 12 will be adhered to the flat underside of the upper portion of the pillow 10, and any remaining base portions will be adhered to another of the base portions 120.

In more detail, as illustrated in FIGS. 1-2, the removable base layers 12, which may or may not be formed of the same material as the upper portion of the pillow 10, according to various example embodiments, are separate bodies that are respectively attached to the upper portion of the pillow 10 or another base layer 12 so as to be stacked on top of one another. One or more of the base layers 12 may be removed, or then re-attached, to adjust the height of the pillow 10. In various example embodiments of the present general inventive concept, at least one of the one or more removable base layers 12 may be configured with at least one inclined surface to adjust an angle of the support surface of the universal pillow.

In the example embodiment illustrated in FIGS. 1-2, the base layers 12 are adhered to the upper portion of the pillow 10 and/or each other by an adhesive compound 13 provided at various points on the base layers 12. The use of an adhesive compound 13 provides a good structural coupling so that the base layers 12 do not easily come off of the rest of the assembly. However, even if one or more of these base layers 12 are removed to lower the height of the pillow 10, the foam material used in some example embodiments lends to re-attachment of the previously detached base layer or layers 12, due to the friction of the material preventing a sheering movement.

Other various example embodiments of the present general inventive concept may provide base layers 12 that are coupled to the upper portion of the pillow 10 and/or one another in different ways. For example, some example embodiments may provide protruding and/or receiving portions that are used to couple the bodies together. In more detail, one side of the base layers 12 may be provided with one or more protruding portions to be received in one or more corresponding receiving portions located on one side of another of the base layers 12. Such receiving portions may also be provided in the flat underside of the pillow 10, and thus the interacting coupling action of all the protruding and receiving portions may allow a flat surface to be maintained on the underside of the pillow 10 as well as one side each of the base layers 12, albeit flat sides with one or more receiving portions, so that the portion resting against a bed or other surface still has a substantially flat contact area.

According to various example embodiments of the present general inventive concept, the base layers 12 may be formed of the same material as the rest of the pillow 10, or may be formed of different materials. In some example embodiments, the base layers 12 themselves may be formed of different materials than one another. In some example embodiments, different ones of the base layers 12 may be provided in different colors to help a user easily distinguish the separation points between the various base layers 12.

In the example embodiment illustrated in FIGS. 1-3, the support surface 11 provided at the top of the pillow 10 includes a frontal/parietal support portion 14 configured to support the forehead (frontal region) of the patient while lying in the prone position, and to support the top portion of the back of the head (parietal region) of the patient while lying in the supine position. Similarly, the support surface 11 includes a mental/occipital support portion 15 configured to support the chin (mental region) of the patient while lying in the prone position, and to support the lower portion of the back of the head (occipital region) of the patient while lying in the supine position. The support surface 11 also includes two respective side portions 16 extending between the frontal/parietal support portion 14 and the mental/occipital support portion 15, and a recessed head receiving portion 17 that is configured to be lower than the frontal/parietal support portion 14, the mental/occipital support portion 15, and the side portions 16. In the example embodiment illustrated in FIGS. 1-3, the recessed head receiving portion 17 is configured to be relatively concave extending from the side portions 16. However, it is noted that the general shape of the recessed head receiving portion 17 is not limited to such a configuration, and may according to various example embodiments have any of a number of configurations that result in a lower surface than the frontal/parietal support portion 14, mental/occipital support portion 15, and side portions 16.

In the example embodiments illustrated in FIGS. 1-3, the frontal/parietal support portion 14 and mental/occipital support portion 15 are separately formed from the rest of the pillow 10, and are configured to be accommodated by, and attached to, end portions of the recessed head receiving portion 17. Such a construction may be implemented to allow an easier formation of the recessed head receiving portion 17 during the construction of the universal pillow 10, but the present general inventive concept is not limited to such a configuration. In various example embodiments, the frontal/parietal support portion 14 and mental/occipital support portion 15 may be formed continuously with rest of the material forming the side portions 19 and the otherwise upper portion of the pillow 10. In various example embodiments in which the frontal/parietal support portion 14 and mental/occipital support portion 15 are separately formed and attached to the pillow 10, either or both of the supporting portions 14-15 may be formed of the same or a different material than other portions of the pillow 10.

In the example embodiment illustrated in FIGS. 1-3, the universal pillow 10 is also provided with access slits 18 configured to extend downward and inward from the side portions 16 to allow access to regions of the patient's anatomy that may be obstructed by the universal pillow 10. For example, in a situation in which the patient is in a prone position, and a device such as an endotracheal tube needs to be used to assist the breathing of the patient, the tube may be routed through one of the access slits 18 to the mouth of the patient. In the example embodiment illustrated in FIGS. 1-3, the access slits 18 are simple cuts in the material forming the pillow 10, but various other example embodiments may include other types of configurations. For example, the access slits 18 may be provided in a U-shape, V-shape, or other shape in which the separated parts of the respective side portions 16 are not immediately adjacent to one another when the pillow is not in use. In other example embodiments of the present general inventive concept, the access slits 18 may be provided in the frontal/parietal support portion 14 and/or mental/occipital support portion 15, in addition to, or in place of, the access slits 18 provided to the side portions 16 illustrated in FIGS. 1-3. Each of the access slits 18 may be configured to accommodate one or more medical devices.

In the example embodiment illustrated in FIGS. 1-3, the recessed head receiving portion 17 is provided with an opening 19 that is configured such that a patient may rest his/her eyes, nose, and/or mouth in the opening 19 so that these parts of the face are not pressed against the surface of the universal pillow 10 when lying in the prone position. According to various example embodiments, one or more of the openings 19 may be formed in the recessed head receiving portion 17 to accommodate these one or more facial regions. The one or more openings 19 may be simply further recessed from the surface of the recessed head receiving portion 17, or may be continuous through the bottom of the portion of the universal pillow 10 that is located above the removable base layers 12. Similarly, although not illustrated in the drawings, the removable base layers 12 may also be provided with one or more openings that correspond to the openings 19 in the upper portion of the universal pillow 10. In the example embodiment illustrated in FIGS. 1-3, the opening 19 includes an orbital opening 20 in which the patient may accommodate the portion of the face located around the eyes, and an oral/nasal opening 21 in which the patient may accommodate the portion of the face located around the mouth and nose. In the example embodiment illustrated in FIGS. 1-3, the orbital opening 20 and oral/nasal opening 21 are areas of one continuous opening 19. However, in various example embodiments the orbital opening 20 may be formed separately from the oral/nasal opening 21. Also, according to various example embodiments, either the oral/nasal opening 21 may be provided without the orbital opening 20, and vice versa. Also, it is noted that while the orbital opening 20 and oral/nasal opening 21 are provided in a rounded "T" shape to form the opening 19 in the example embodiment of FIGS. 1-3, the present general inventive concept is not limited to any such shape and/or configuration.

FIGS. 4-5 illustrate example uses of the universal pillow 10 of FIGS. 1-3. FIG. 4 illustrates a patient 40 using the universal pillow 10 while lying on an operating table 42 in the supine position, and FIG. 5 illustrates the patient 40 using the universal pillow 10 while lying on the operating table 42 in the prone position. The height of the universal pillow 10 may be adjusted by removing one or more of the removable base layers 12. Such adjustability allows the universal pillow 10 to be used with patients of varying sizes. The flat bottom provides increased stability. The density of the foam reduces pressure related tissue injury. The increased coefficient of friction of the foam reduces slipping, thus provides a more stable platform. According to various procedures, the universal pillow 10 may be used in conjunction with other pillows and/or rolls. In the example embodiment illustrated in FIG. 5, support rolls 52 that run longitudinally from the clavicle of the patient to the iliac crest have been provided to allow the patient to enjoy increased comfort and support during the medical procedure.

While the example embodiment illustrated in FIGS. 4-5 again shows the universal pillow 10 as having two removable base portions 12, it is understood that the height of the universal pillow 10 may be adjusted by providing more or less removable base layers 12 according to the patient's needs. The frictional nature of the foam material facilitates the ability to re-attach the removable base layers 12 as needed, enabling quick and easy height adjustment without slippage of the device or patient. Also, as illustrated in FIGS. 4-5, and as previously described, the access slit 18 is able to accommodate a medical device such as an endotracheal tube 50 while the patient is comfortably accommodated in a prone position by the universal pillow 10. In other various example embodiments, the universal pillow 10 may be provided without the access slits 18.

According to various example embodiments of the present general inventive concept, a universal pillow is provided to accommodate the head of a patient in a prone and/or supine position. Different example embodiments of the present general inventive concept provide several benefits over the conventional approaches. For example, the relatively inexpensive construction and material used in the foam embodiment of the universal pillow affords single patient use of the roll, which decreases or eliminates cross-contamination and risk of patient dermatologic reaction to reusable positioner cleaning solution residue, which may be used on pillows formed of gel or other material, while reducing room turnover time. The typical current cleaning protocol for gel or other reusable positioners stipulates a specific drying time after the cleaning solution is applied, and a water rinse to then remove the cleaning solution residue prior to patient use. In cases in which such a protocol is not followed with those types of positioners, the risk of cross-contamination is highly increased. In cases in which the water rinse is not followed, then a dermatologic reaction to the cleaning solution residue can occur. Association of periOperative Registered Nurses (AORN) Standards and Practices dictate that rolled towels, blankets, sheets, or I.V. bags not be used for such purposes, as they are not considered to be positioning devices.

Further, due to the adjustable nature of the universal pillow according to various example embodiments of the present general inventive concept, the universal pillow may be adjusted to fit various body types and/or situations. And when constructed of foam, as discussed in regard to various example embodiments in this description, the density of the foam allows for support without significant tissue pressure injury. The foam also has an increased coefficient of friction to decrease slipping of the universal pillow, and the stability may be further increased by having a flat "bottom". It is understood that the "bottom" simply refers to the surface of the universal pillow that is adjacent to a resting surface relative to the portion of a patient being supported by the universal pillow, such as an operating table, as the universal pillow has no required orientation facing up, down, or otherwise in the conventional sense.

It is noted that the simplified diagrams and drawings do not illustrate all the various connections and assemblies of the various components, however, those skilled in the art will understand how to implement such connections and assemblies, based on the illustrated components, figures, and descriptions provided herein, using sound engineering judgment.

Numerous variations, modifications, and additional embodiments are possible, and accordingly, all such variations, modifications, and embodiments are to be regarded as being within the spirit and scope of the present general inventive concept. For example, regardless of the content of any portion of this application, unless clearly specified to the contrary, there is no requirement for the inclusion in any claim herein or of any application claiming priority hereto of any particular described or illustrated activity or element, any particular sequence of such activities, or any particular interrelationship of such elements. Moreover, any activity can be repeated, any activity can be performed by multiple entities, and/or any element can be duplicated.

While the present general inventive concept has been illustrated by description of several example embodiments, it is not the intention of the applicant to restrict or in any way limit the scope of the inventive concept to such descriptions and illustrations. Instead, the descriptions, drawings, and claims herein are to be regarded as illustrative in nature, and not as restrictive, and additional embodiments will readily appear to those skilled in the art upon reading the above description and drawings.

The invention claimed is:

1. A universal pillow to accommodate a head of a patient in a prone and in a supine position, comprising:

a support surface having a frontal/parietal support portion, a mental/occipital support portion, and two side portions extending between respective ends of the frontal/parietal and mental/occipital support portions;

a recessed head receiving portion provided in the support surface, the recessed head receiving portion having a convex surface extending below top surfaces of each of the frontal/parietal support portions, mental/occipital support portions, and side portions, the convex surface having an opening configured to receive at least a portion of a face of the patient; and a bottom surface disposed opposite to the support surface, wherein the frontal/parietal support portion and the mental/occipital support portion are substantially semicircular and are each removably attachable to the convex surface and have rounded surfaces that are configured to be accommodated by opposing end portions of the convex surface such that when the frontal/parietal support portion and the mental/occipital support portions are attached to the respective end portions of the convex surface, the lowest point of the convex surface is at the same level as the lowest point of the rounded surfaces, respectively.

2. The universal pillow of claim 1, wherein the opening extends through the bottom surface.

3. The universal pillow of claim 1, wherein the opening includes an orbital opening and/or an oral/nasal opening.

4. The universal pillow of claim 1, wherein the opening includes an orbital opening and an oral/nasal opening, the oral/nasal opening being substantially perpendicular to the orbital opening.

5. The universal pillow of claim 1, further comprising access slits provided in the side portions to allow access to the patient for one or more medical devices.

6. The universal pillow of claim 1, further comprising one or more removable base layers provided to the bottom surface to adjust a height of the universal pillow.

7. The universal pillow of claim 6, wherein the support surface, recessed head receiving portion, bottom surface, and/or one or more removable base layers are formed from a foam material having a high coefficient of friction to inhibit slippage therebetween.

8. The universal pillow of claim 6, wherein the one or more removable base layers include at least two removable base layers coupled to the bottom surface in a stack such that a first one of the removable base layers is coupled to the bottom surface, and a second one of the removable base layers is coupled to the first removable base layer.

9. The universal pillow of claim 6, wherein the one or more removable base layers are coupled to the bottom surface and/or one another by an adhesive compound.

10. The universal pillow of claim 6, wherein the one or more removable base layers are coupled to the bottom surface and/or one another by protruding and/or receiving portions provided to the bottom surface and removable base layers.

11. The universal pillow of claim 1, wherein the universal pillow is formed of a foam fabricated from polyurethane foam, foam rubber, XPS foam, polystyrene, phenolic material, or any combination thereof.

* * * * *